(12) United States Patent
Nakamura

(10) Patent No.: US 7,572,012 B2
(45) Date of Patent: Aug. 11, 2009

(54) OPTICAL ELEVATION APPARATUS

(75) Inventor: Yukitsugu Nakamura, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 229 days.

(21) Appl. No.: 11/694,211

(22) Filed: Mar. 30, 2007

(65) Prior Publication Data
US 2007/0236658 A1      Oct. 11, 2007

(30) Foreign Application Priority Data
Apr. 11, 2006    (JP)    ............................ 2006-108233

(51) Int. Cl.
*A61B 3/00*    (2006.01)
(52) U.S. Cl. ...................................... 351/245
(58) Field of Classification Search .......... 351/244–245
See application file for complete search history.

(56) References Cited

U.S. PATENT DOCUMENTS

| 4,015,892 | A | * | 4/1977 | Tabata | 359/212 |
| 4,310,224 | A | * | 1/1982 | Weilbach et al. | 351/225 |
| 5,116,114 | A |   | 5/1992 | Nakamura et al. | 351/205 |
| 5,777,344 | A | * | 7/1998 | Hayashi | 351/245 |
| 5,974,743 | A | * | 11/1999 | Vaia | 52/169.6 |
| 7,159,984 | B2 | * | 1/2007 | Fukuma et al. | 351/227 |
| 7,467,871 | B2 | * | 12/2008 | Lawhorn et al. | 351/245 |
| 2004/0089097 | A1 | * | 5/2004 | Savard | 74/567 |

FOREIGN PATENT DOCUMENTS

JP          7-363          1/1995

* cited by examiner

*Primary Examiner*—Jordan M. Schwartz
(74) *Attorney, Agent, or Firm*—Fitzpatrick, Cella, Harper & Scinto

(57) ABSTRACT

A guide roller projects from the side surface of an optical system body. The optical system body is held to be elevatable within a predetermined range along an arcuate guide member. A weight balancing means incorporating a spring attaches to the lower corner on the side surface of the optical system body. A hook attaches to one end of the arcuate guide member. A pulley attaches to the upper end of the arcuate guide member. One end of a wire fixes to the hook. The spring of the gravity balancing means pulls the wire through the pulley.

5 Claims, 6 Drawing Sheets

PRIOR ART

OPTICAL ELEVATION APPARATUS

BACKGROUND OF THE INVENTION

1. Field of the Invention

The present invention relates to an optical elevation apparatus which elevates an optical system body within a predetermined angular range about a fixed point on the optical axis of an objective lens as a rotation center.

2. Description of the Related Art

For example, a fundus camera serving as an ophthalmic device employs an optical elevation apparatus which vertically elevates the optical axis of an objective lens about a fixed point in the vicinity of the pupil of an eye under examination as a rotation center in order to observe or take an image of the fundus of the eye under examination and its periphery. In such a conventional optical elevation apparatus, generally, an arcuate guide member having the fixed point as the center elevatably holds the fundus camera body.

The arcuate guide member is provided with, for example, an arcuate rack gear. A pinion gear meshing with the rack gear is rotated through a manipulation handle to elevate the fundus camera body.

Japanese Patent Laid-Open No. 7-000363 discloses a buffer means for canceling the gravitational force of a fundus camera body so as to reduce the manipulation force required for elevation.

In Japanese Patent Laid-Open No. 7-000363, as shown in FIG. 6, a buffer 3 is used as a means for balancing the gravity. The buffer 3 cancels the gravitational force of a fundus camera body 1, having a weight of about 10 kg, along an arcuate guide member 2. The buffer 3, however, has a drawback in that it largely projects from the side surface of the fundus camera body 1.

SUMMARY OF THE INVENTION

It is an object of the present invention to provide an optical elevation apparatus with a compact outer appearance, which solves the above problem and avoids a gravity balancing means from extending outwardly from an optical system main body.

Further features of the present invention will become apparent from the following description of exemplary embodiments with reference to the attached drawings.

DESCRIPTION OF THE EMBODIMENTS

The present invention will be described in detail with reference to the embodiments shown in FIGS. 1 to 5.

First Embodiment

Figure 1:
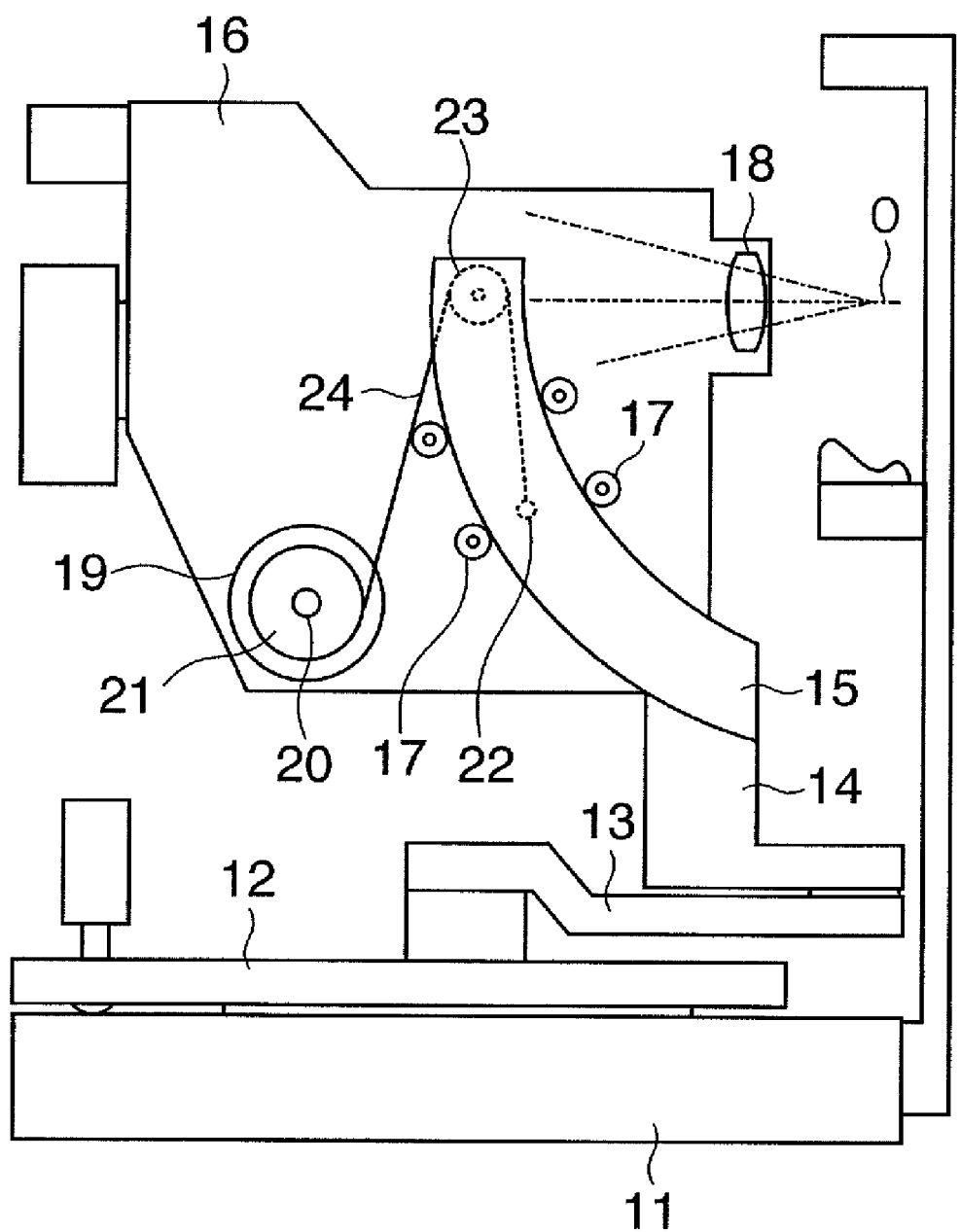
FIG. 1 is a side view of a fundus camera according to the first embodiment.
Figure 2:
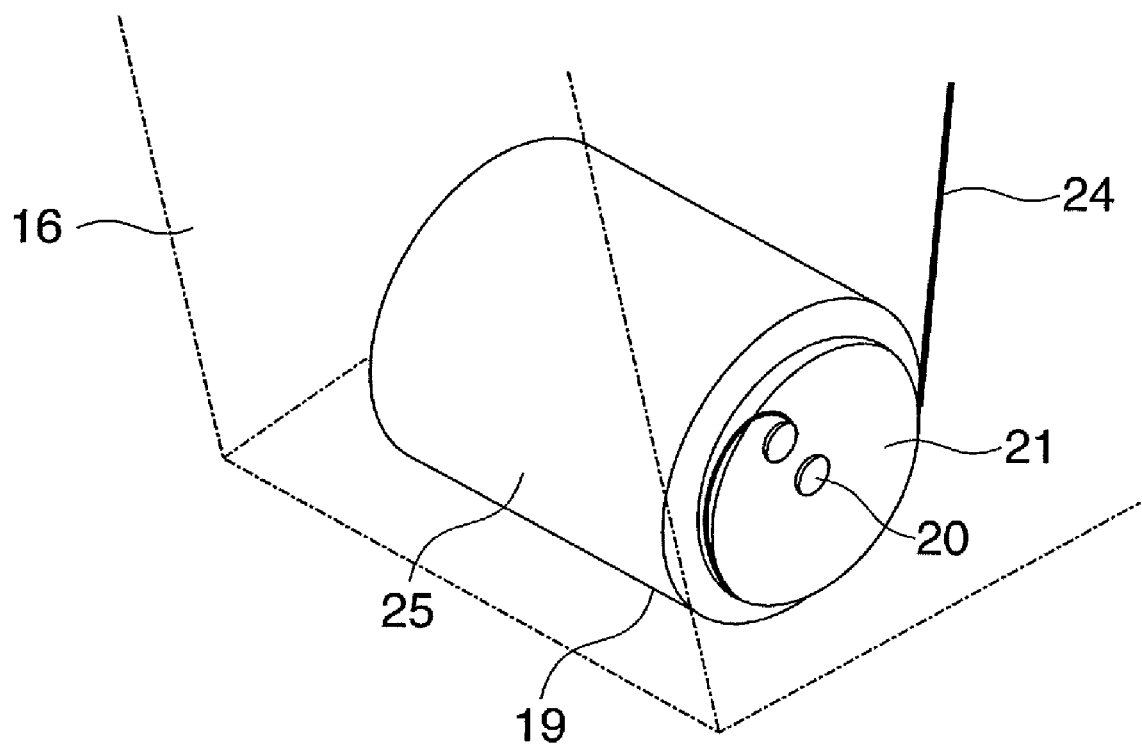
FIG. 2 is a main part enlarged perspective view.

FIG. 1 is a side view of a fundus camera according to the first embodiment, and FIG. 2 is a main part enlarged perspective view. An arm holding member 13 attaches to a base 11 of a fundus camera through a stage 12. An arcuate guide member 15 fixes to the arm holding member 13 through an arm 14. The arcuate guide member 15 supports an optical system body 16. For example, four guide rollers 17 project from the side surface of the optical system body 16. The radius of arc of the arcuate guide member 15 is set such that the arcuate guide member 15 elevates the optical system body 16 vertically about a fixed point O on the extension of the optic axis of an objective lens 18 as a rotation center. The optical system body 16 is held to be pivotal within a predetermined range of about 10° to 15° both upward and downward along the arcuate guide member 15 through the guide rollers 17.

The arcuate surfaces on the two sides of the arcuate guide member 15 respectively have V-shaped grooves, and the outer surfaces of the guide rollers 17 form inverted-V shapes, respectively. The inverted-V shapes of the guide rollers 17 slide along the V-shaped grooves of the arcuate guide member 15. Thus, the optical system body 16 can swing in the elevating direction with a light force without moving in a direction outward from the side surface of the optical system body 16.

A gravity balancing means 19 using a coil spring attaches to the lower corner of the side surface of the optical system body 16. The gravity balancing means 19 comprises a take-up drum 21 attached to a rotating shaft 20, and a coil spring (not shown).

A hook 22 fixes to the side surface of the optical system body 16 on the inner side of the arcuate guide member 15. A pulley 23 rotatably attaches to the inner side of the upper end of the arcuate guide member 15. One end of a wire 24 serving as a tractive cord member fixes to the hook 22. The wire 24 runs between the arcuate guide member 15 and optical system body 16, extends in the optical system body 16 through the pulley 23, and is pulled by the gravity balancing means 19.

FIG. 2 is an enlarged perspective view of the gravity balancing means 19. The interior of the optical system body 16 is provided with a coil spring storing housing 25 (spring unit). The rotating shaft 20 of the take-up drum 21 which takes up the wire 24 is rotatably held in the coil spring storing housing 25. The coil spring winds around the rotating shaft 20. The coil spring requires a strong traction force to balance against the force of the optical system body 16, which has a weight of about 10 kg and moves downward under gravity. The gravity balancing means 19 may be arranged on one side in the optical system body 16, or on each of the two sides in the optical system body 16.

According to the first embodiment, as the gravity balancing means 19 pulls the wire 24 through the pulley 23, the pulley 23 serves as a movable pulley from the principle of dynamics. Accordingly, the force that pulls the wire 24 theoretically becomes ½, and the gravity balancing means 19 can be made compact. When the coil spring storing housing 25 is made compact, the optical system body 16 can accommodate it within its width. Thus, the coil spring storing housing 25 will not project through the side surface of the optical system body 16.

A coil spring force adjusting means (not shown) may be provided so the gravitational force of the optical system body 16 can accurately balance with the force required to pull the optical system body 16 upward against the downward force. With the adjustment of the spring coil force adjusting means, the operator can elevate the optical system body 16 by only pushing part of it manually without requiring a manipulation handle for elevation. Although the optical system body 16 desirably stops still at the position where the operator releases it, where necessary, an elevating locking means may be provided.

Second Embodiment

Figure 3:
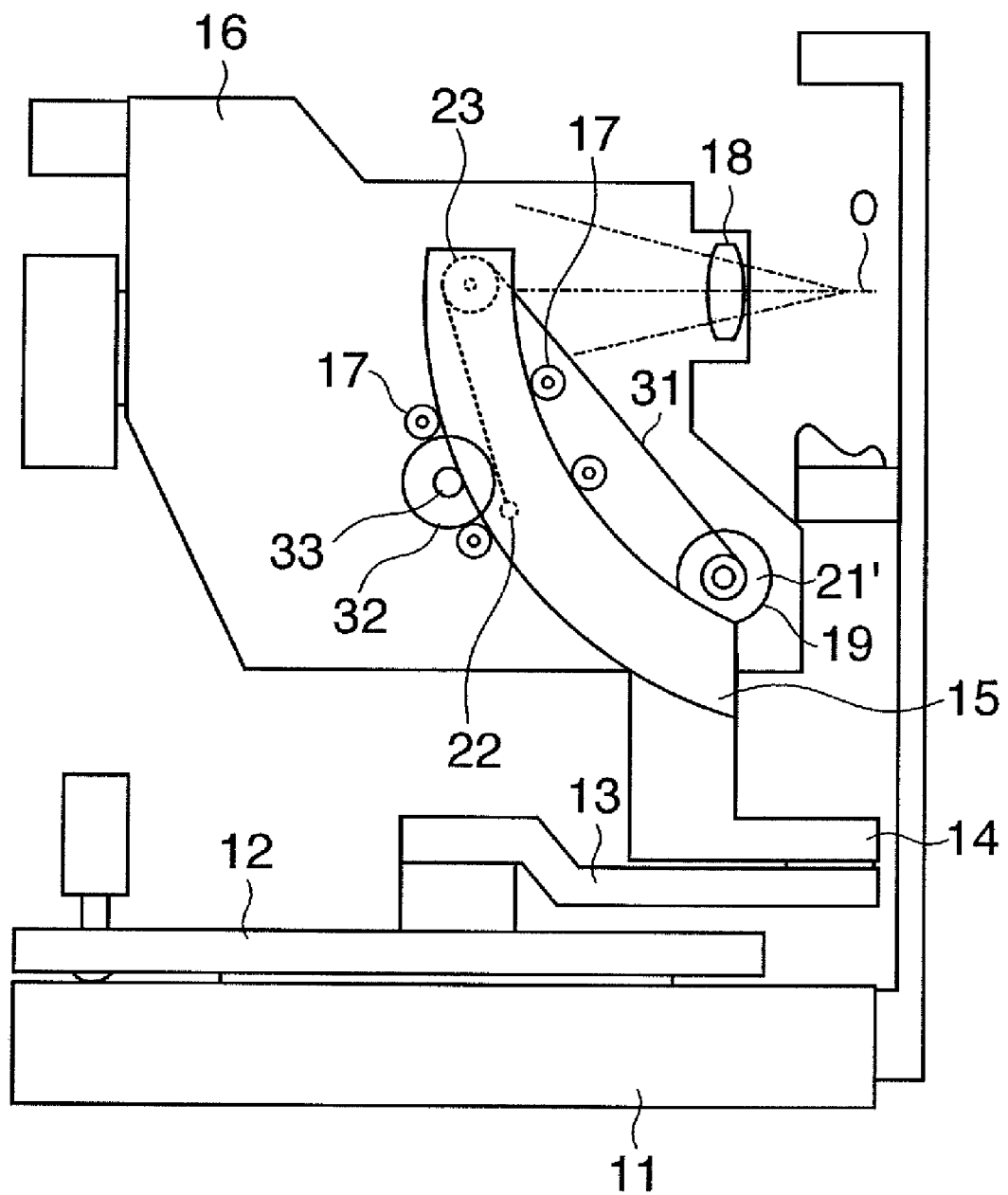
FIG. 3 is a side view of a fundus camera according to the second embodiment.

FIG. 3 shows a side view of a fundus camera according to the second embodiment. In FIG. 3, the same members as in the first embodiment are denoted by the same reference numerals. A gravity balancing means 19 may fix to any portion of an optical system body 16 provided that from such a location it can pull a wire 24 returned by a pulley 23.

According to the second embodiment, as shown in FIG. 3, the gravity balancing means 19 fixes to a lower corner on an objective lens 18 side where the gravity balancing means 19 will not hinder the manipulation. To further downsize the gravity balancing means 19, if the take-up diameter of a take-up drum 21' incorporating a coil spring is decreased to increase the take-up rotation frequency, the spring force of the coil spring (not shown) can be decreased. Furthermore, if a belt 31 formed of a thin band-like elastic metal plate or the like is used in place of the wire 24, it can be conveniently wound around the take-up drum 21' in multiple turns.

According to the above embodiment, if the gravitational force of the optical system body 16 and the pulling force of the gravity balancing means 19 balance accurately, elevating manipulation can be performed with a light manipulation force. For example, when the elevating manipulation is to be performed through a manipulation handle 32 (expressed by an outer circle), if urging a friction pulley 33 (expressed by an inner circle indicated by an alternate long and short dashed line) against the arcuate surface of an arcuate guide member 15 and rotating the friction pulley 33, the friction force generated between the friction pulley 33 and arcuate guide member 15 can elevate the optical system body 16. Thus, a pinion gear and rack gear as in the conventional case become unnecessary.

Third Embodiment

Figure 4:
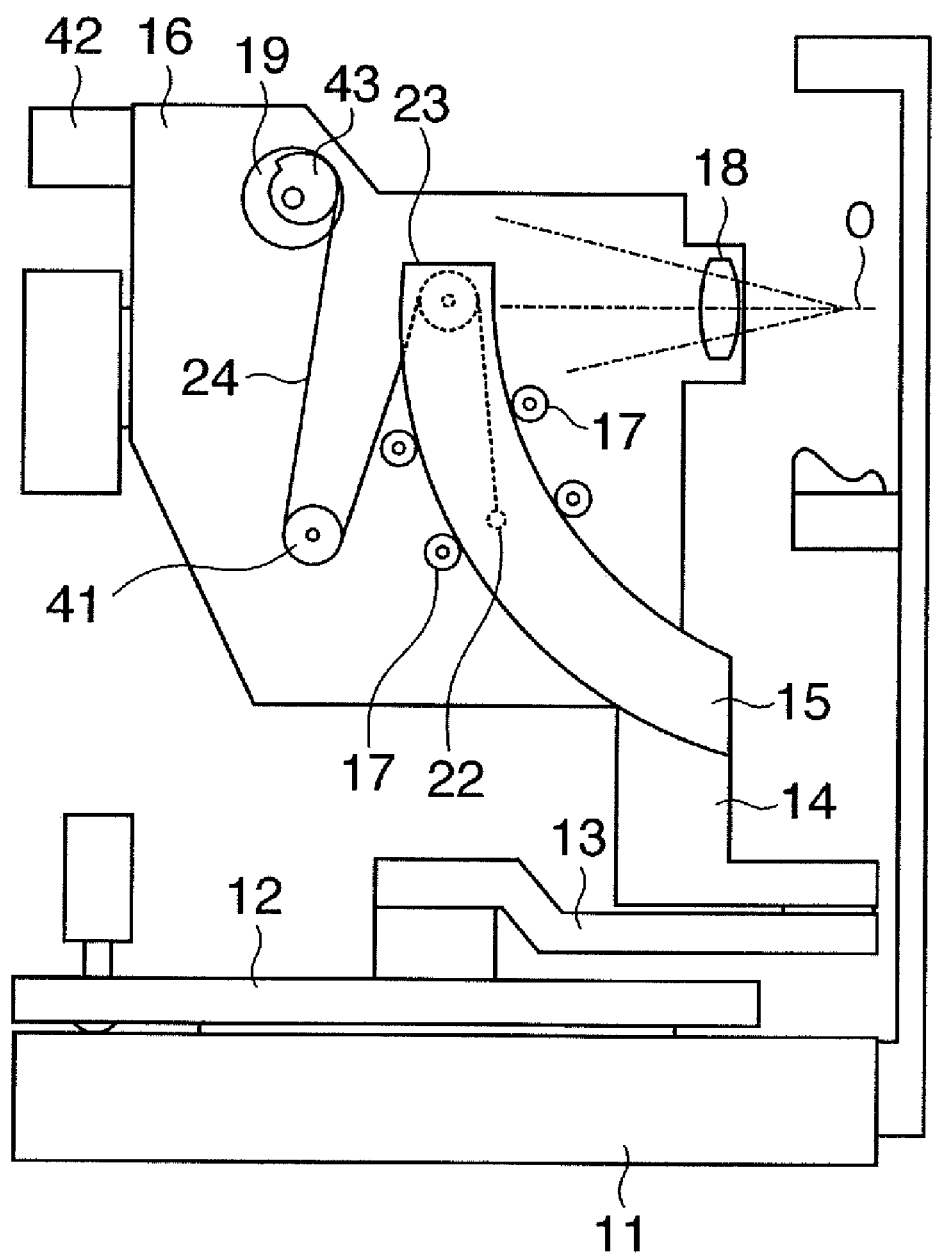
FIG. 4 is a side view of a fundus camera according to the third embodiment.

FIG. 4 is a side view of the third embodiment and shows a modification of the first embodiment. A wire 24 is pulled through a return pulley 41 arranged on the side surface of an optical system body 16. A gravity balancing means 19 is arranged near an eyepiece 42 in the optical system body 16. By intervening the return pulley 41 in this manner, there are more possible positions to attach the gravity balancing means 19, and the force balancing performance of the gravity balancing means 19 can be improved.

When vertically elevating the optical system body 16 along an arcuate guide member 15, the gravitational force of the optical system body 16 is not constant but varies depending on the elevation angle, and the force of the coil spring also varies in accordance with the spring characteristics accompanying the take-up angle. According to the third embodiment, in order to correct variations in these forces, a cam-type take-up drum 43 with a cam-type outer shape takes up the wire 24. The distance from the rotation center to the outer surface of the cam-type take-up drum 43 changes gradually in accordance with the winding angle. Thus, the required torque force to take up the wire 24 changes in accordance with the rotation angle. The cam shape of the cam-type take-up drum 43 is desirably optimal so the varying characteristics of the force acting on the wire 24 complement the varying characteristics of the take-up torque force.

Fourth Embodiment

Figure 5:
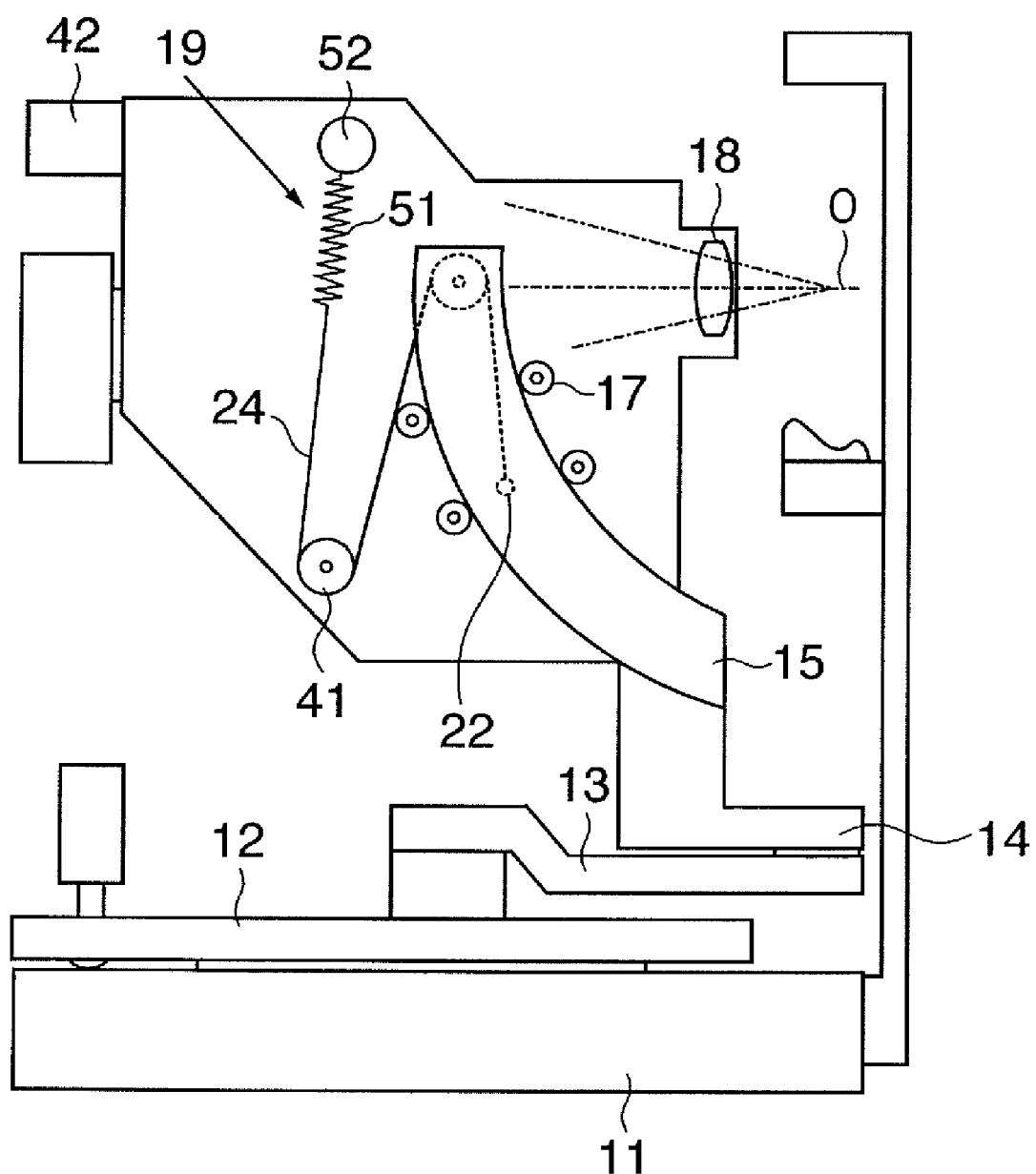
FIG. 5 is a side view of a fundus camera according to the fourth embodiment.
Figure 6:
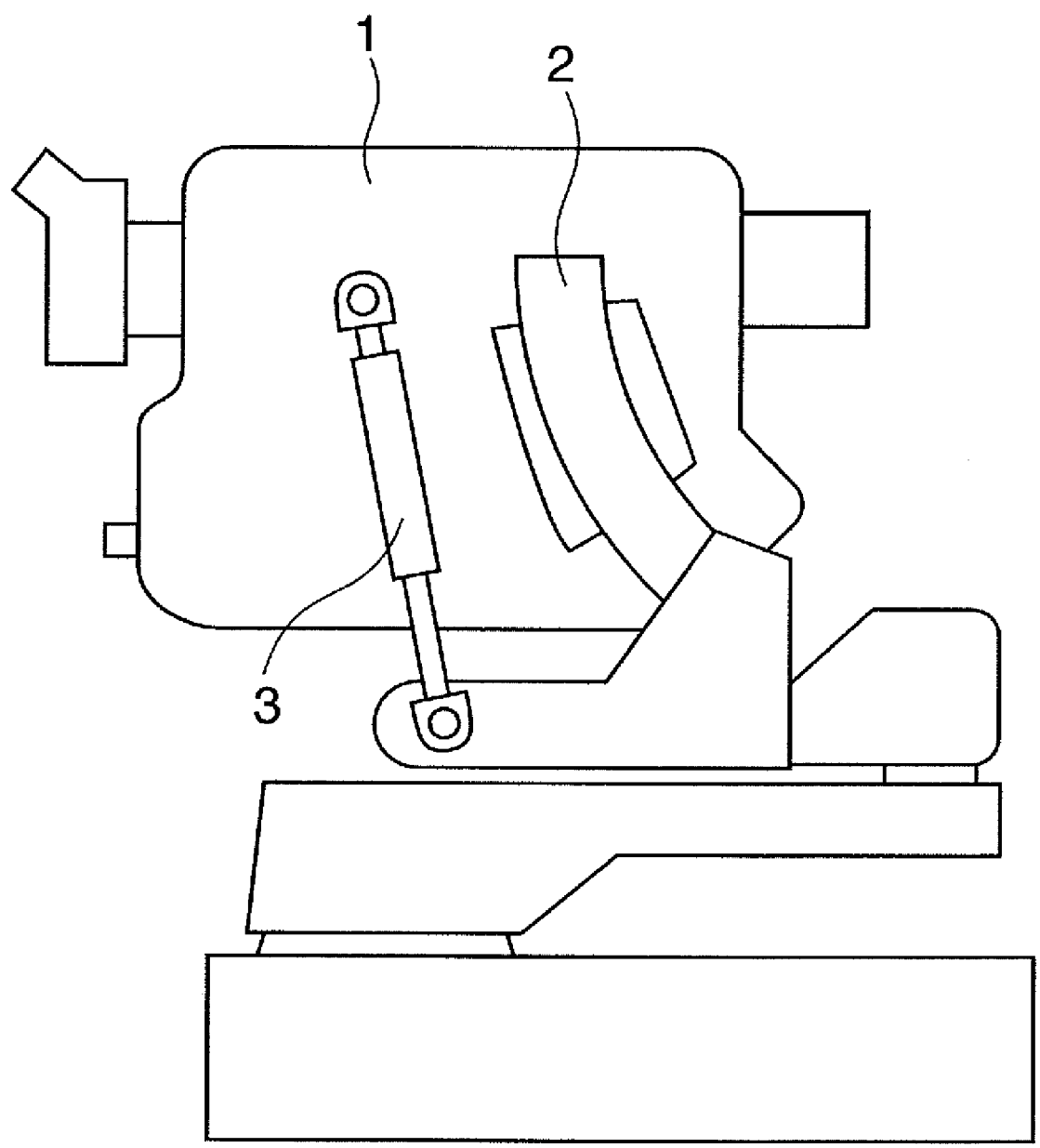
FIG. 6 is a side view of a conventional fundus camera.

FIG. 5 is a side view of a fundus camera according to the fourth embodiment. In FIG. 5, a gravity balancing means 19 employs a tensile coil spring 51. One end of a wire 24 returned by a return pulley 41 is connected to one end of the tensile coil spring 51. The other end of the tensile coil spring 51 catches on a hook 52 fixing to the inner side of an optical system body 16.

To arrange an elongated tensile coil spring 51, a sufficiently large space is required in the optical system body 16. According to the fourth embodiment, the degree of freedom in direction to pull the wire 24 by using the return pulley 41 is large. This allows free choice of the position of the tensile coil spring 51.

Although the above embodiments exemplify a fundus camera as an ophthalmic device, the present invention is not limited to this. For example, in place of the fundus camera, the present invention can be applied to other optical elevation apparatuses such as a slit lamp microscope, a device that radiates a laser beam to the fundus of an eye under examination, or a tomographic imaging device for the interior of the retina.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Patent Application No. 2006-108233, filed Apr. 11, 2006, which is hereby incorporated by reference herein in its entirety.

What is claimed is:

1. An optical elevation apparatus for elevating an optical system body, comprising:
    an optical system body adapted to elevate around a predetermined fixed point of the optical elevation apparatus;
    a guide member adapted to guide an elevation of the optical system body;
    a hook provided to the guide member and adapted to fix one end of a traction cord member;
    a spring unit provided to the optical system body and adapted to take up the traction cord member to generate a traction force; and
    a pulley for the traction cord member, which is provided to the guide member,
    wherein the pulley is arranged inside the guide member such that the traction cord member runs through the optical system body.

2. The apparatus according to claim 1, wherein the traction cord member loops around the pulley provided to the guide member and then around a pulley provided to the optical system body to change a pulling direction.

3. An optical elevation apparatus for elevating an optical system body, comprising:
    an optical system body adapted to elevate around a predetermined fixed point of the optical elevation apparatus;
    a guide member adapted to guide an elevation of the optical system body;
    a hook provided to the guide member and adapted to fix one end of a traction cord member;
    a spring unit provided to the optical system body and adapted to take up the traction cord member to generate a traction force; and
    a pulley for the traction cord member, which is provided to the guide member,
    wherein the spring unit comprises a take-up drum whose shape is a cam shape, and a distance between an outer surface to a center position of the take-up drum varies in accordance with a rotation angle, to compensate for variations in force of the optical system body to move downward in accordance with an elevation angle and a change in force of the gravity balancing means due to spring characteristics.

4. The apparatus according to claim 1, wherein the traction cord member comprises one of a wire and a belt.

5. An optical elevation apparatus for elevating an optical system body, comprising:
- an optical system body adapted to elevate around a predetermined fixed point of the optical elevation apparatus;
- a guide member adapted to guide an elevation of the optical system body;
- a hook provided to the guide member and adapted to fix one end of a traction cord member;
- a spring unit provided to the optical system body and adapted to take up the traction cord member to generate a traction force; and
- a pulley for the traction cord member, which is provided to the guide member,
- wherein said optical system body further comprises an objective lens, and
- said optical system body adapted to elevate around said predetermined fixed point which predetermined fixed point is on an extension of optical axis of the objective lens.

* * * * *